United States Patent [19]

Elert

[11] Patent Number: 4,555,935
[45] Date of Patent: Dec. 3, 1985

[54] APPARATUS FOR PRESSURE TESTING OF CAN BODIES AND LIDS

[75] Inventor: Karl Elert, Grosse Pointe Park, Mich.

[73] Assignee: The Stroh Brewery Company, Detroit, Mich.

[21] Appl. No.: 546,168

[22] Filed: Oct. 27, 1983

[51] Int. Cl.[4] .............................................. G01M 3/02
[52] U.S. Cl. .......................................... 73/52; 73/37; 73/49.2
[58] Field of Search .................... 73/52, 49.3, 49.2, 37, 73/45.2, 45.4

[56] References Cited

U.S. PATENT DOCUMENTS

| 900,324 | 10/1908 | Swangren | 73/49.3 |
|---|---|---|---|
| 983,962 | 2/1911 | Werner | 73/52 |
| 1,118,478 | 11/1914 | Dixon | 73/49.2 |
| 2,527,560 | 10/1950 | Maher | 73/49.2 |
| 2,696,106 | 12/1954 | Schneider | 73/49.2 |
| 2,737,803 | 3/1956 | Doudera, Jr. et al. | 73/52 |
| 3,196,665 | 7/1965 | Quackenbush | 73/37 |
| 3,418,845 | 12/1968 | Helms | 73/49.2 |
| 3,958,448 | 5/1976 | Willis et al. | 73/52 |
| 4,194,388 | 3/1980 | Mack | 73/37 |

FOREIGN PATENT DOCUMENTS 71696 of 1953 Netherlands ............................ 73/52

Primary Examiner—Stewart J. Levy
Assistant Examiner—Hezron E. Williams
Attorney, Agent, or Firm—Andrus, Sceales, Starke & Sawall

[57] ABSTRACT

An apparatus for pressure testing a can body. The apparatus includes a housing having a pivotable cover and an empty can with the lid attached is placed in a cradle in the housing. As the cover is moved to the closed position, a hollow needle, operably connected to the cover, is automatically inserted through the wall of the can body. On locking of the cover in the closed position, an electric circuit can be established to introduce gas under pressure through the needle into the can body. A readout of the pressure required to bulge the can body is given, thereby indicating whether the can body meets manufacturing specifications.

15 Claims, 6 Drawing Figures

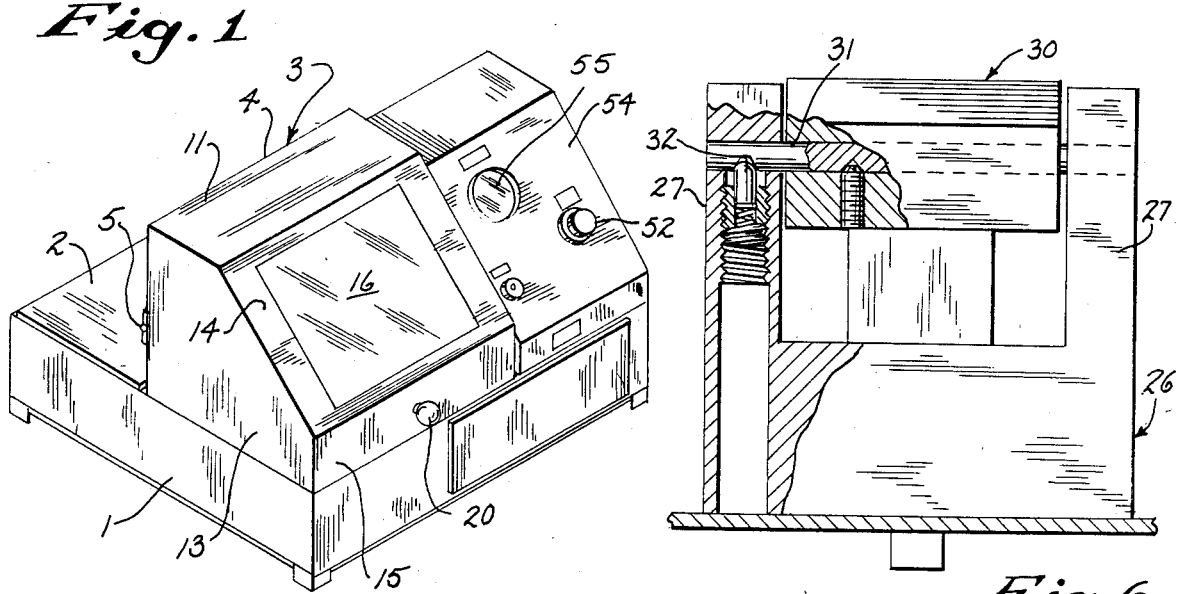
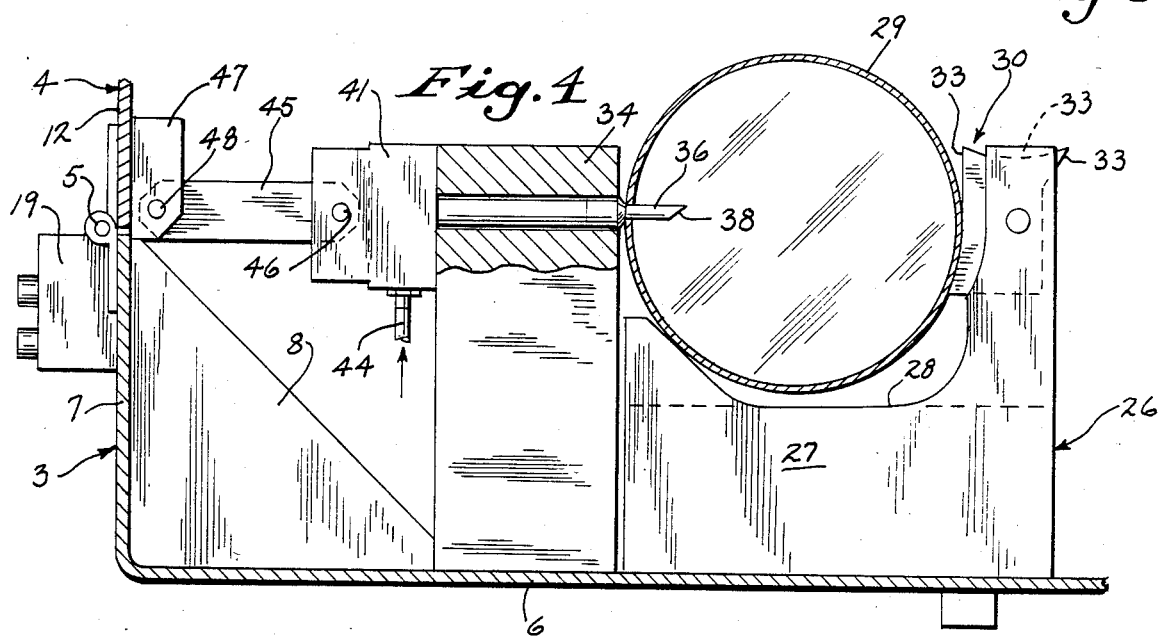
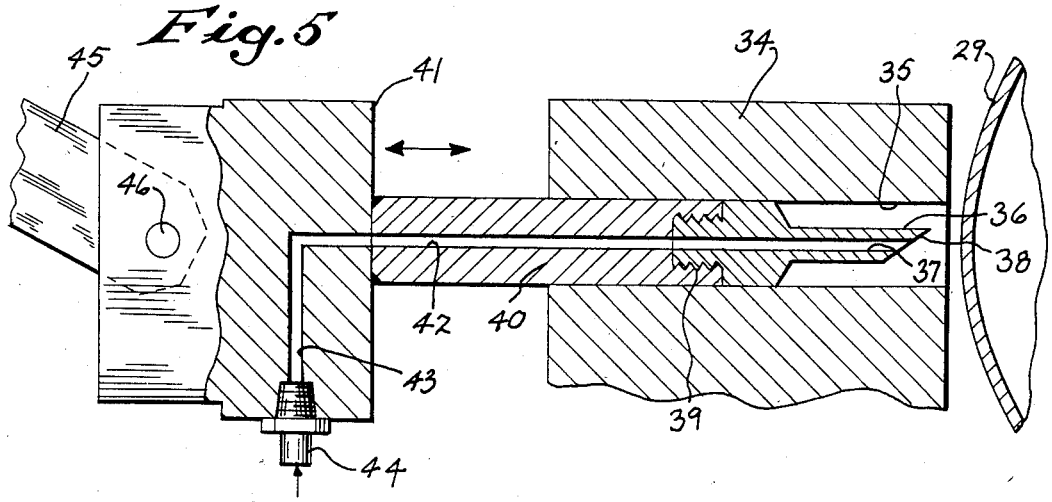

APPARATUS FOR PRESSURE TESTING OF CAN BODIES AND LIDS

BACKGROUND OF THE INVENTION

In the manufacture of beverage cans, such as aluminum beer cans and soft drink cans, the open-ended can bodies are periodically tested to determine whether they meet manufacturing specifications. In the usual practice, a run of can bodies is removed from the line several times a day and pressure tested. In the past, the testing procedure has consisted of clamping the open-ended can body on a short cylindrical mandrel and air under pressure is introduced through the mandrel into the can body. The operator visually observes when the can bulges under pressure and notes this pressure reading. The testing of lids was done in a similar manner, but requires a fixture separate from that used to test the can-bodies.

With the testing method as used in the past, if the can body was not fully aligned and sealed to the mandrel, the gas pressure could unseat the can body from the mandrel causing the can body to flip out of the clamping fixture. To prevent this, in some cases a bar was extended across the closed end of the can body, but the bar tended to interfere with bulging of the can bottom, so that erroneous readings of pressure were occasionally obtained.

SUMMARY OF THE INVENTION

The invention is directed to an improved apparatus for pressure testing of can bodies, such as aluminum can bodies used for beer and soft drinks as well as the lids. In accordance with the invention, the apparatus includes a housing having a pivotable cover. An empty can body with a lid attached is placed horizontally in a cradle within the housing. As the cover is moved to the closed position, a needle, operably connected to the cover, is automatically inserted through the wall of the can body. By locking the cover in the closed position, an electrical circuit is established so that gas can be introduced under pressure through the needle into the can body. When the can body on the seamed lid bulges, a pressure readout is obtained to determine whether the can meets manufacturing specifications.

The apparatus of the invention, in contrast to prior methods, tests the empty can body with a seamed lid and this more nearly equates with the finished can condition.

The can testing method of the invention is fully automatic in that the can is punctured by the needle as a consequence of moving the lid or cover to the closed position. This insures that the can body will be completely enclosed during the pressurization operation to eliminate any possible damage or injury to the operator.

The testing apparatus of the invention removes the human element from testing and provides a precise indication of the pressure required to bulge the can body, thereby providing a more accurate representation of the physical properties of the can body.

Other objects and advantages will appear in the course of the following description.

DESCRIPTION OF THE DRAWINGS

The drawings illustrate the best mode presently contemplated of carrying out the invention.

In the drawings:

FIG. 1 is a perspective view of the apparatus for testing the can bodies with the cover in the closed position;

FIG. 4 is an enlarged vertical section showing the can body puncturing assembly;

FIG. 5 is a fragmentary enlarged vertical section showing the details of the can body puncturing assembly; and FIG. 6 is an end view of FIG. 4 with parts broken away and showing the saddle which engages the can body.

DESCRIPTION OF THE ILLUSTRATED EMBODIMENT

Figure 2:
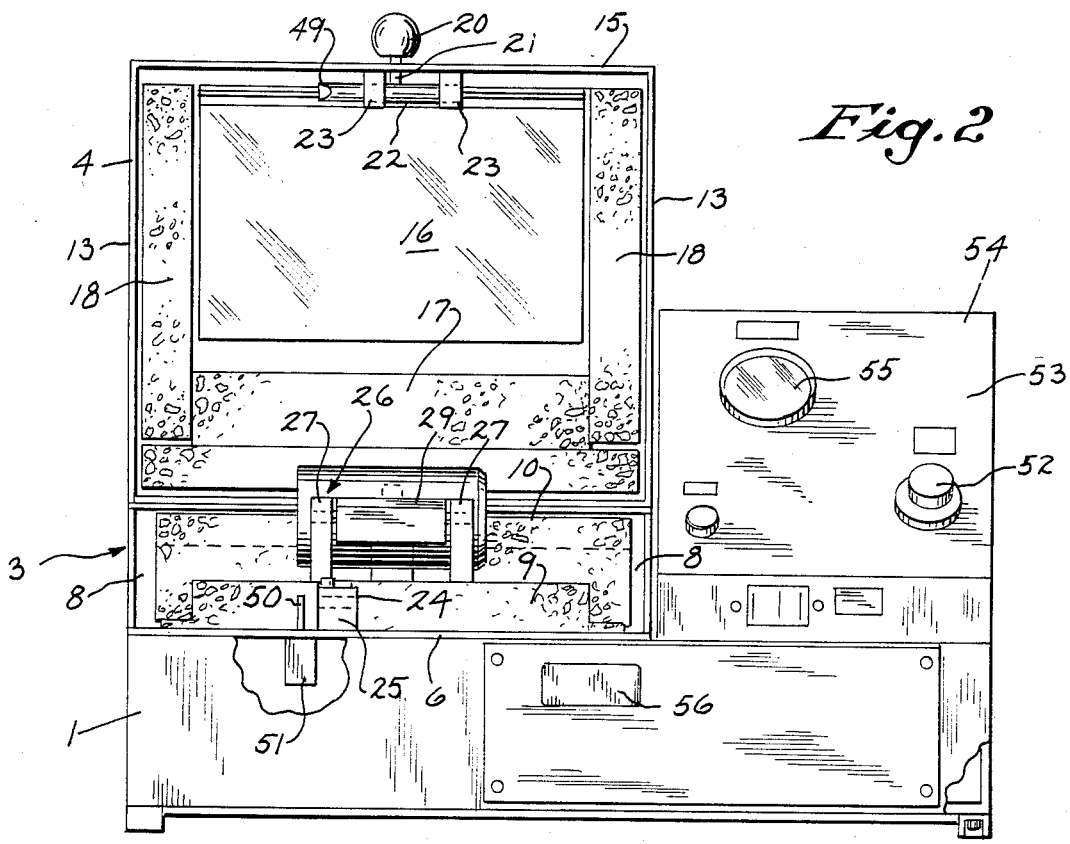
FIG. 2 is a front elevation of the apparatus with the cover in the open position.

The apparatus for pressure testing of can bodies includes a base 1 having an upper surface 2. A housing 3 is supported on the forward portion of base 1 and the open upper end of housing 3 is adapted to be enclosed by a cover 4 which is pivoted to housing 3 by hinge 5. Cover 4 can be moved between an open position, as shown in FIGS. 2 and 3, to a closed position, as shown in FIG. 1.

Figure 3:
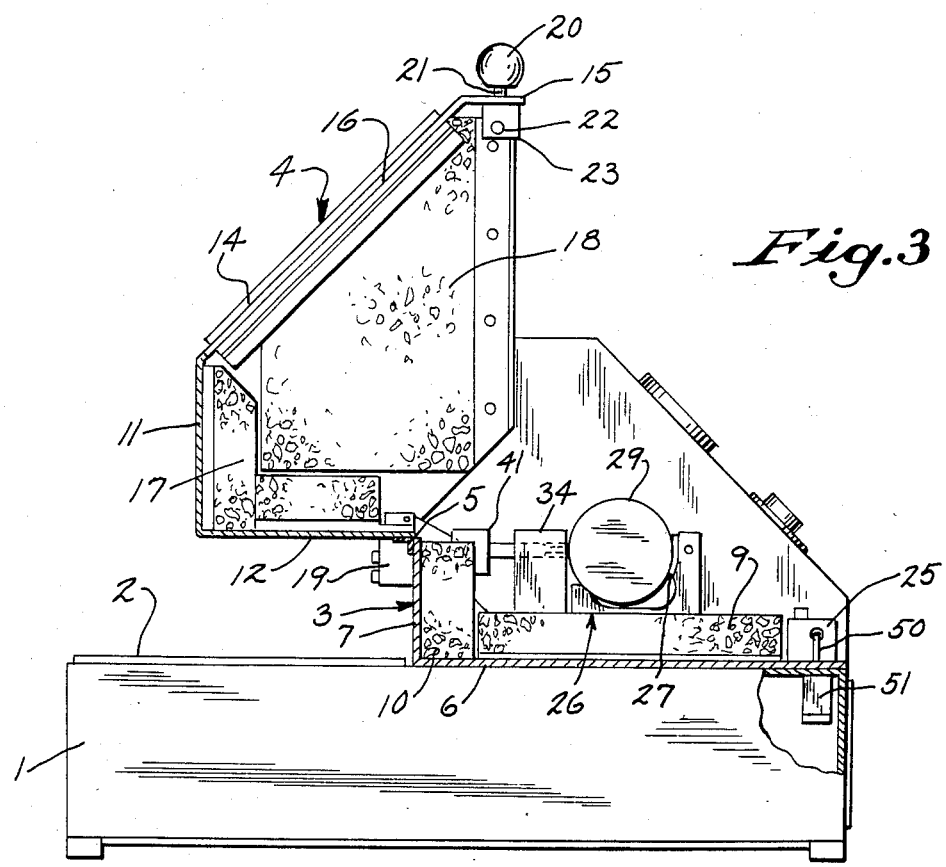
FIG. 3 is a side view of the apparatus shown in FIG. 2.

As shown in FIGS. 2 and 3, housing 3 includes a bottom 6, a rear wall 7, and a pair of triangular side members 7 that connect the bottom wall and rear wall 8. A layer of sound insulation 9 is located on bottom wall 6 and similarly, a layer of sound insulation 10 extends across the rear wall 7.

The pivotable cover 4 includes a top 11, a rear wall 12, which extends downwardly from the rear edge of top 11, and a pair of side walls 13 which connect the top and rear wall. In addition, cover 4 includes a sloping front wall 14 which terminates in a vertical front wall 15. In order to view the testing operation carried on within the housing, a transparent window 16 is provided in sloping front wall 14.

As in the case of the housing 3, cover 4 is lined with sound insulation. More particularly, a layer of sound insulation 17 is applied to top wall 11 and layers of insulation 18 are also applied to side walls 13.

Cover 4 can be pivoted between an open position, as shown in FIGS. 2 and 3, to a closed position, as shown in FIG. 1. To limit the pivotal movement of the cover when in the open position, one or more stop blocks 19, shown best in FIG. 4, are secured to the outer surface of rear wall 7 and the rear wall 12 of cover 4 will engage the stop to limit the open position, as shown in FIG. 3.

To lock the cover 4 in the closed position, a locking knob 20 is located on the outer surface of wall section 15 and is connected by stem 21 to a slide bolt 22, best shown in FIG. 2. Slide bolt 22 is adapted to slide within brackets 23 secured to the inner surface of front wall 15, and the end of slide bolt 22 is received within a hole 24 in latch block 25 mounted on bottom wall 6 of the housing. By sliding the knob laterally, bolt 22 will be engaged with hole 24 to lock the cover in the closed position.

Positioned within the housing is a cradle 26 composed of a pair of side members 27, each having an upwardly facing curved surface 28. A closed can body 29 having a lid attached is adapted to be placed in the cradle 26 for testing. A rotatable saddle 30 is mounted between the side members 27. As shown in FIG. 6, a shaft 31 extends between side members 27 and passes through an opening in saddle 30. A set screw in saddle 30 engages shaft 31 and spring loaded detents 32 mounted within openings in side members 27 engage recesses in shaft 31 to maintain the saddle in the desired position. As shown in FIG. 4, the saddle is provided with a plurality of surfaces 33 each of which has a different curvature to conform to the curvature of the body 29 being tested. Depending upon the size of the can bodies being tested, the saddle can be swiveled or rotated to have the desired surface 33 face toward the center of cradle 26 and detent 32 will retain the saddle in the proper position.

To test the can body 29, a gas, such as air under pressure, is introduced into the can body and when the pressure within the can body reaches an elevated value, the can body will bulge or deform and the apparatus of the invention will give a visual readout of the pressure at the time of bulging to determine whether the can body meets the manufacturing specifications.

Gas is introduced into the can body 29 by a can body puncturing assembly, including a block 34 that is mounted on bottom wall 6 of housing 3. Block 34 has a passage 35 and a hollow needle 36 containing central passage 37 is mounted for sliding movement within passage 35. As shown in FIG. 5, the outer end 38 of needle 36 is formed a sharpened tip 38 that is adapted to puncture the can body, as illustrated in FIG. 4, while the inner end of needle 36 is threaded within an axial opening 39 in shaft 40. The outer end of shaft 40 is attached to block 41. As shown in FIG. 5, shaft 40 is provided with an axial passage 42 which communicates with passage 37 in needle 36 and the opposite end of passage 42 establishes communication with a passage 43 in block 41. As shown in FIGS. 4 and 5, an air line 44, connected to a suitable source of air or gas under pressure, is connected to passage 43. With this connection, air under pressure will be delivered through line 44, passage 43, passage 42, to the central passage 37 of needle 36 and then into the interior of can body 29.

A provision is made to automatically cause needle 36 to penetrate the can body 29 when the cover 4 is moved from the open to the closed position. In this regard, one end of a link 45 is pivoted to the outer end of block 41 by pivot pin 46, while the opposite end of link 45 is pivoted to block 47 attached to rear wall 12 of cover 4 by pivot pin 48. As shown in FIGS. 3 and 5, when the cover is in the open position, the tip 38 of needle 36 will be substantially flush with the vertical outer surface of block 34. When the cover is pivoted to the closed position, the linkage 45 will slide the needle 36 in a direction toward saddle 30, thereby causing the tip 38 of needle 36 to penetrate the wall of can body 29. Thus, the invention provides an automatic penetration of the can wall with operation of the cover. This not only speeds up the testing operation, but insures that the cover will be in a closed position when the pressure testing is carried out.

After the cover has been moved to the closed position, and the needle 36 has penetrated can body 29, the locking knob 20 is moved laterally causing the slide bolt 22 to engage the hole 24 in latch block 25 to lock the cover in the closed position. Moving the slide bolt to the locked position also causes the tapered end 49 of the latch bolt to engage the arm 50 of switch 51 mounted on bottom wall 6. Actuation of the switch 51 will establish the necessary electrical circuitry to enable air under pressure to be introduced through air line 44 to the can body 29 when the "start" button 52, located on panel 53 of housing 54, is depressed.

As shown in FIG. 1, a standard pressure gauge 55 to indicate the incoming pressure is also mounted on panel 53 and a digital pressure readout 56 is located in base 1 which gives a readout of the pressure within the can body.

In operation, can body 29, having a closed bottom and a lid seamed to the opposite end, is placed in cradle 26. Cover 4 is then moved to the closed position causing needle tip 38 to penetrate the can body. By locking the slide bolt 22, the switch 51 is actuated to establish the electrical circuitry to deliver air under pressure to the can body when the "start" button 52 is depressed.

The pressure within the can body 29 will progressively increase as a linear or straight line function and when any portion of the can body or lid bulges, the linear function is interrupted. This interruption of the linear function, as determined by a conventional electro-pneumatic transducer located in air line 44, will generate a signal to lock in the digital readout of pressure, as shown at 56, and will release the pressure in the line. The digital readout of the pressure will remain until the next cycle, when depressing of the "start" button 52 will reset the system. The operator can then determine whether this pressure at the instant of bulging falls within the manufacturing specifications.

After the pressure testing, cover 4 is unlocked through operation of locking knob 20 and by moving the cover to the open position, the needle will be automatically withdrawn from the can body, so that the can body can be removed and discarded.

The invention provides a fully automatic mechanism for pressure testing of can bodies which eliminates the human element and provides precise readings of the pressure required to bulge the can body.

As the can bodies are tested with a seamed lid, the testing eliminates the need for separate testing fixtures for the can body and lid. Furthermore, the testing more nearly equates with the finished can conditions than testing operations which test the open ended can body without an attached lid.

The mechanism is completely safe, in that it requires that the cover be in the closed and locked condition before pressure is introduced into the can body. This eliminates any possibilities of injury to the operator.

Various modes of carrying out the invention are contemplated as being within the scope of the following claims particularly pointing out and distinctly claiming the subject matter which is regarded as the invention.

I claim:

1. An apparatus for the pressure testing of closed can bodies, comprising a housing having an open portion, a cover to enclose said open portion and being movable between an open position and a closed position, can body supporting means disposed within the housing for supporting a can body to be tested, can penetrating means disposed within the housing, actuating means operable as a consequence of the cover moving from the open position to the closed position for actuating said can penetrating means to cause said can penetrating means to penetrate the wall of the can body, and gas supply means for introducing a gas under pressure through said can penetrating means into said can body.

2. The apparatus of claim 1, wherein said can body support means comprises a cradle.

3. The apparatus of claim 1, wherein said can penetrating means is mounted for movement between an inoperative position wherein said can penetrating means is located out of contact with the can body positioned in said can body support means and an operative position wherein said can penetrating means penetrates the wall of said can body, said actuating means moving said can penetrating means between the inoperative and operative positions.

4. The apparatus of claim 1, wherein said open portion is an open top and said cover is hinged to said housing.

5. The apparatus of claim 3, wherein said actuating means comprises a linkage interconnecting the cover and said can penetrating means.

6. The apparatus of claim 1, wherein said can penetrating means includes a needle having a sharpened tip disposed to penetrate the wall of the can body.

7. The apparatus of claim 1, and including locking means for locking the cover to the housing and movable between a locked position and an unlocked position.

8. The apparatus of claim 7, and including means responsive to the locking means moving to the locked position for activating said gas supply means.

9. An apparatus for the pressure testing of empty can bodies, comprising a housing having an open side, a cover to enclose said open side and movable between an open position and a closed position, support means disposed within the housing to support a closed empty can body to be tested, a can penetrating member disposed within the housing and adapted to penetrate the wall of a can body supported on said support means, means for mounting said can penetrating member for movement between an inoperative position and an operative position wherein said can penetrating member penetrates the wall of the can body, actuating means operably connected to the can penetrating member and responsive to the cover being moved toward the closed position for moving said penetrating member from the inoperative position to the operative position, locking means for locking the cover to the housing and having a locked position and an unlocked position, gas supply means for introducing gas through the can penetrating member into said can body, and means responsive to the locking means being moved to the locked position for activating said gas supply means.

10. An apparatus for pressure testing of empty can bodies, comprising a housing having an opening therein, a cover to enclose the opening and movable between an open and a closed position, support means disposed within the housing for supporting an empty can body to be tested, a hollow can penetrating member having a sharpened tip disposed within the housing and movable between an inoperative position where said sharpened tip is out of contact with said can body supported on said support means and an operative position wherein said sharpened tip penetrates the wall of the can body, actuating means for moving the can penetrating member between the inoperative and operative positions, gas supply means for introducing gas through said can penetrating member into the can body, and means responsive to the cover being in the closed position for activating said gas supply means and supplying gas into said can body.

11. The apparatus of claim 9, wherein said actuating means comprises a linkage interconnecting the cover and said can penetrating member.

12. The apparatus of claim 9, wherein said can penetrating member is a hollow needle.

13. The apparatus of claim 10, wherein said means for moving the can penetrating member is operably connected to the cover and is operable as a consequence of the cover being moved from the open position toward the closed position.

14. The apparatus of claim 9, wherein said support means includes a rotatable saddle to engage the wall of the can body, said saddle having a plurality of curved surfaces, each having a curvature to complement the curvature of different diameter can bodies.

15. The method for the pressure testing of can bodies, comprising the step of placing a closed empty can body to be tested in a support in a housing having an open portion, said open portion adapted to be enclosed by a cover, moving the cover from the open to the closed position, penetrating a hollow needle through the wall of the can body as a consequence of moving the cover from the open to the closed position, locking the cover in the closed position, introducing gas under pressure through said needle into the can body, said gas causing the can body to be deformed, and determining the pressure required to cause said deformation.

* * * * *